(12) United States Patent
Jorgensen et al.

(10) Patent No.: US 9,731,847 B2
(45) Date of Patent: Aug. 15, 2017

(54) METHOD FOR HOLDING MULTIPLE TYPES OF DIAGNOSTIC TEST CONSUMABLES IN A RANDOM ACCESS SINGLE CONTAINER

(71) Applicant: Ortho-Clinical Diagnostics, Inc., Raritan, NJ (US)

(72) Inventors: Jens H. Jorgensen, Rochester, NY (US); Joseph Wycallis, Pittsford, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 783 days.

(21) Appl. No.: 13/710,857

(22) Filed: Dec. 11, 2012

(65) Prior Publication Data
US 2014/0163920 A1 Jun. 12, 2014

(51) Int. Cl.
*B01L 3/00* (2006.01)
*B65B 5/06* (2006.01)
*G01N 35/04* (2006.01)

(52) U.S. Cl.
CPC .............. *B65B 5/06* (2013.01); *B01L 3/545* (2013.01); *G01N 2035/0436* (2013.01); *G01N 2035/0439* (2013.01); *G01N 2035/0493* (2013.01)

(58) Field of Classification Search
USPC ............. 705/28, 1, 22; 422/64, 65; 210/362; 382/195; 235/451
See application file for complete search history.

(56) References Cited

U.S. PATENT DOCUMENTS

| | | | | |
|---|---|---|---|---|
| 5,374,395 A | * | 12/1994 | Robinson | G01N 21/253 422/562 |
| 5,512,432 A | | 4/1996 | Lapierre et al. | |
| 5,578,269 A | * | 11/1996 | Yaremko | G01N 35/025 210/361 |
| 6,259,654 B1 | * | 7/2001 | de la Huerga | A61J 7/0084 368/10 |
| 7,263,501 B2 | * | 8/2007 | Tirinato | G06Q 10/087 360/27 |
| 7,938,324 B2 | | 5/2011 | Tamarkin et al. | |
| 2002/0086417 A1 | * | 7/2002 | Chen | B01L 3/5027 435/287.3 |
| 2003/0031599 A1 | * | 2/2003 | Brown | G01N 33/4875 422/501 |

(Continued)

OTHER PUBLICATIONS

Chinese Office Action for CN 201310675162.0; dated: Sep. 2, 2016; 12 pages.

*Primary Examiner* — Vanel Frenel
(74) *Attorney, Agent, or Firm* — Barclay Damon, LLP (57) ABSTRACT

An immunodiagnostic test method includes holding a selection of immunological test elements or consumables in one or more containers attached to or positioned in the analyzer and providing random access to any test element therein. The container can hold multiple types of test elements in compartments or slots. Through sensing of a test element position in its slot, the detection mechanism of the invention provides for random access to multiple types of test elements in any sleeve and within a single sleeve, and provides efficient inventory control. The method increases the number of test element types that may be loaded onto an analyzer and maintains fast determination of inventory.

13 Claims, 9 Drawing Sheets

(56) References Cited

U.S. PATENT DOCUMENTS

| | | |
|---|---|---|
| 2003/0148530 A1* | 8/2003 | Lauks .................... G01N 33/49 |
| | | 702/23 |
| 2004/0181528 A1 | 9/2004 | Tirinato et al. |
| 2010/0106624 A1 | 4/2010 | Ashrafzadeh et al. |
| 2010/0150779 A1* | 6/2010 | Chow .................. G01N 35/025 |
| | | 422/64 |
| 2012/0178170 A1 | 7/2012 | Van Praet |
| 2014/0038222 A1* | 2/2014 | Alt .......................... G01N 21/63 |
| | | 435/29 |
| 2016/0054316 A1* | 2/2016 | Egan .................. G01N 21/6486 |
| | | 506/9 |

\* cited by examiner

METHOD FOR HOLDING MULTIPLE TYPES OF DIAGNOSTIC TEST CONSUMABLES IN A RANDOM ACCESS SINGLE CONTAINER

FIELD OF THE INVENTION

The application relates to the field of immunodiagnostic testing using an automated analyzer and in particular to a method and device for holding a selection of immunological test elements or consumables in one or more containers attached to or placed into the analyzer and providing random access to any test element therein. The container is conveniently in the form of a sleeve, or rack that may be placed in a drawer adjacent and connected to the loading area of the analyzer. Such container can hold multiple types of test elements in compartments or slots. Through sensing of a test element position in its slot, the detection mechanism of the invention provides for random access to multiple types of test elements in any sleeve and within a single sleeve, and further provides efficient inventory control. Thus the method increases the number of test element types that may be loaded onto an analyzer while maintaining fast determination of inventory.

BACKGROUND OF THE INVENTION

Immunological agglutination reactions are currently used for identifying various kinds of blood types as well as for detecting various kinds of antibodies and antigens in blood samples and other aqueous solutions. In such procedures, a sample of red blood cells is mixed with serum or plasma in a consumable device such as a test tubes, microplates or in the method knows in the art as column agglutination technology (CAT), a card or cassette tube configuration, wherein the mixture is incubated and then centrifuged. Various reactions then occur or do not occur depending on, for example, the blood types of the red blood cells or whether certain antibodies are present within the blood sample. These reactions manifest themselves as clumps of cells or as particles with antigens or antibodies on their surfaces, referred to as agglutinates. The failure of any agglutinates to appear indicates no reaction has occurred, while the presence of agglutinates, depending on the size and amount of the clumps formed, indicates the presence of a reaction and the level of concentration of cells or antibodies in the sample and reaction strength.

As described, for example, in U.S. Pat. No. 5,512,432 to LaPierre et al., an agglutination test method has been developed and successfully commercialized, which method employs gel or glass bead microparticles contained within a small column, referred to as a microcolumn or a microtube. The said microcolumn or microtube is arranged as one of a plurality of columns formed in a transparent card or cassette format wherein multiple such tubes containing reagents are molded into a single consumable. A reagent, such as anti-A, is dispensed in a diluent in the microcolumns of the card or cassette and test red blood cells are placed in the reaction chamber above the column. The column, as part of the entire card or cassette, is then centrifuged. The centrifugation accelerates the reaction, if any, between the red blood cells and the reagent, and also urges any cells toward the bottom of the column. In the meantime, the glass beads or the gel material acts as a filter, and resists or impedes downward movement of the particles in the column. As a result, the nature and distribution of the particles in the microcolumn provides a visual indication of whether any agglutination reaction has occurred, and if such a reaction has occurred, the strength of the reaction based on the relative position of the agglutinates in the column. If no agglutination reaction has occurred, then all or virtually all of the red blood cells in the microtube will pass downward during the centrifugation procedure, to the bottom of the column in the form of a pellet. Conversely and if there is a strong reaction between the reagent and the red blood cells, then virtually all of the red blood cells will agglutinate, and large groupings will form at the top of the microtube above the gel or bead matrix in that the matrix is sized not to let these clumps pass through. Reactions falling between these latter two extremes are possible in which some but not all of the red blood cells will have agglutinated. The percentage of red blood cells that agglutinate and the size of the agglutinated particles each have a relationship with the strength of the reaction. Following the centrifugation process and after all processing steps have been completed, the microtube is visually examined by either a human operator or by machine vision such as a CCD camera for imaging the resulting reaction between the red blood cells and the reagent which is then classified. The reaction is classified as being either positive or negative, and if positive, the reaction is further classified into one of four classes depending on the strength of the reaction.

Figure 1:
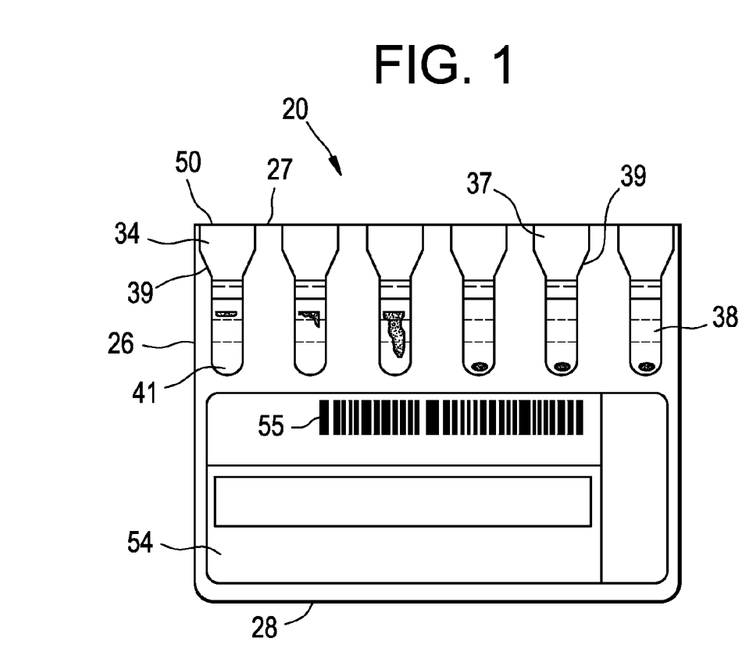
FIGS. 1 and 2 are front views of a pair of prior art immunodiagnostic test elements.
Figure 2:
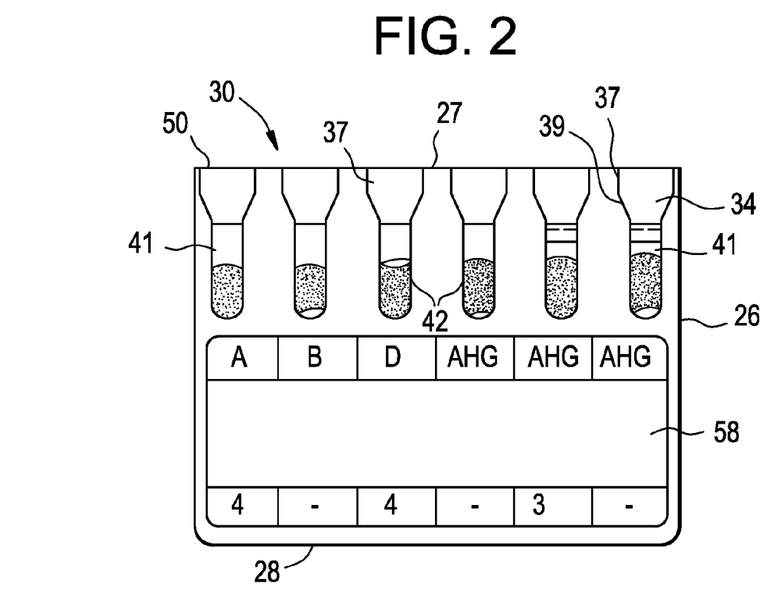

Currently, clinical immunohematology utilizes so-called gel cards and/or glass bead cassettes which are known consumable test elements and employ a plurality of microtubes for purposes of creating agglutination reactions as described above for blood grouping, blood typing, antigen or antibody detection and other related applications and uses. Thus, multiple types of test elements are known for the various blood grouping, typing and antigen antibody tests. These consumable test elements commonly include a planar substrate that supports a plurality of transparent columns or microtubes, each of the columns containing a quantity of an inert material, such as the aforementioned gel material or glass beads, respectively, that is coated with an antigen or antibody or material or is provided with a carrier-bound antibody or antigen, each of the foregoing being provided by the manufacturer. A pierceable wrap completes the assembly of the test element. This wrap which may be for example in the form of an adhesively or otherwise—attached foil wrap, covers the top side of the test element to cover the contents of each column. This same foil wrap conveniently provides a reflective surface which is utilized in the method of the instant invention as detailed hereinbelow. Once the covering wrap is pierced, aliquots of patient sample and possibly reagents (e.g., if reagents are not first added by the manufacturer or additional reagents, depending on the test) can be added to the columns, either manually or using automated apparatus. The test element thus containing patient sample (e.g., red blood cells and sera) is then incubated and following incubation, the test element is spun down by centrifugation, as noted above, in order to accelerate an agglutination reaction that can be graded either based on the position of agglutinates within each transparent column of the test element or cassette or due to a lack of agglutination based on the cells settling at the bottom of the test column. As shown in FIGS. 1 & 2, also present on the test element 20, 30 is typically located a barcode 55 bearing information identifying the reagents for the immunohematologic test type for that test element. Other barcode information on the test element can include shelf expiration, lot number, and the sequence of that test element within a given manufacturer's lot, among any other indicating information as desired by the manufacturer.

A number of automated or semi-automated apparatus, such as those manufactured by Ortho-Clinical Diagnostics, Inc., DiaMed A.G., Bio-Rad, and Grifols, are known that utilize a plurality of test elements in the form of gel cards or bead cassettes, such as those manufactured and sold by Micro-Typing Systems, Inc., DiaMed A.G., and BioRad, among others. Currently, test elements for a single immunological assay type are obtained from the manufacturer arranged in containers such as boxes or sleeves having multiple such cards or cassettes in separate slots. These boxes or sleeves conveniently fit in lanes of a slide tray in a drawer which is part of the analyzer. Depending on analyzer type, size and capacity, the slide tray in the drawer of an analyzer may accommodate from five (5) to twelve (12) such lanes separated by rails, permitting from five (5) to twelve (12) sleeves to be accommodated in an analyzer. Each container (sleeve) may contain for example twenty (20) cards or cassettes. This physical space limitation for sleeves and sleeve capacity restricts the types of immunological test element types to a maximum of twelve (12), one type per sleeve. However, there are currently about fifteen (15) to twenty (20) different test element (cards or cassettes) types available for use in blood analysis testing, for example including various manufacture-available ABO blood-type and blood antibody-type test element cards/cassette types. Thus the requirement for operator intervention to insert and exchange specific cards upon physician order is high. The operator or technician using the apparatus must therefore load the appropriate sleeve containing the desired cards or cassettes, which requires opening the card/cassette loading area (CCLA) of the apparatus and manually inserting into a slot within the sleeve the one or more desired cards or cassettes for the appropriate immunological test(s). Such manual interaction by the operator with the analyzer requiring opening the analyzer drawer to access the sleeves and changing the test element necessarily interrupts the blood testing process and delays results.

As described, each of the consumable test elements includes a top side adhesive wrap. This wrap conveniently comprises a foil wrap which covers the microcolumns and forms a seal relative to the contents of the microcolumns further preventing microcolumn contents from drying out or degrading. To allow for inventory control, analyzers made by the above-mentioned companies are equipped with software permitting detection functionality to determine which consumable or test element (card or cassette) positions are in fact loaded with a consumable test element and of which type. In one aspect of the invention, an optical proximity sensor detects the reflective difference between the presence and absence of the foil wrapped consumable test element. An algorithm in the sub-processor of the apparatus thus determines the inventory for the consumable test element of a given type.

Following optical sensing of all sleeves within the clinical analyzer apparatus, and when all slots in a sleeve contain the same type test element, inventory of particular test element types is quickly performed by a gripper in the analyzer picking a single consumable test element from each sleeve and reading with a barcode reader or camera system of the type that will be familiar to one having skill in the relevant art, to determine the type of test element loaded in the entire sleeve. However, such methodology does not permit more than one type of test element per sleeve. Since picking every consumable test element in the sleeve to determine the consumable type would make inventory function too slow for practical use, the instant invention is directed to a method and container to provide a flexible inventory determination of multiple types of test elements in a single sleeve. This avoids the need to swap out sleeves to introduce test elements of different types.

SUMMARY OF THE INVENTION

According to one aspect, the invention is directed to a method of determining an inventory of test elements of multiple types stored in a clinical analyzer comprising sensing test elements within a group of test elements in a container containing multiple groups of test elements wherein a gap capable of being sensed and detected is provided between each group of test elements of a single type, generating data from said sensing, and using the data to provide an inventory of the multiple test elements. The presence or absence of test elements within their slots is detected by proximity sensing. The container may be in the form of a box or sleeve, and the detectable gap is a one or a multiple of slot(s) where a test element(s) would normally be located. The type of test element within the group of test elements is then determined by sensing at least one of the elements within each group of test elements such as for example by a barcode reader or a camera useful for the purpose that reads the barcode on the test element. Such determination of the test element type is performed when the container is initially placed in the clinical analyzer and when the analyzer is powered on. Multiple methods of sensing may be employed for example optical sensing, and the result of the sensing is stored in a processing subsystem. The data is generated by performing an algorithm that determines a change in number of test elements in the group in the sleeve from previously stored data in the number of test elements in the group in the sleeve, preferably clinical blood assay consumables having a foil wrap on their top side surface. The clinical blood assay consumable is preferably an immunohematology card or cassette.

In another embodiment of the invention, there is provided an invention for retrieving a previous indication of the number of test elements in the group in the container, determining a change in the number of test elements in the group in the container to a new number of test elements in the group in the container in the step of generating, associating the change in the number of test elements in the group in the container to a usage indication, and storing the association in the procession subsystem. By use of a graphical user interface on the apparatus, an operator may conveniently be provided with an indication of the change in the number of test elements in the group in the container, by visual or audible indication. In each case, the container may be a sleeve, a rack, or a support with positioning guides for holding the test element(s) in place in the slide tray of the drawer.

In yet a further embodiment of the invention there is provided a method for providing random access to multiple types of consumables in a container, comprising arranging each type of consumable or test elements in a group within slots within the container, and spacing each group of test elements apart from another group of test elements of a different test type by a detectable gap, which detectable gap is conveniently one or more than one empty slot(s) in the container. The container is conveniently in the form of a sleeve or box, a rack, or a support having positioning guides for holding test element, having slots to accommodate the test elements. The test elements are preferably clinical blood assay consumables such as an immunohematologic agglutination assay cards or cassettes, which display a foil wrap on their top side surface. Detection of the gap is achieved by proximity sensing of the reflective difference between the presence and absence of the foil wrapped consumable in a given slot.

In yet a further embodiment of the invention there is supplied a container comprising multiple types of test elements each being arranged together according to their type, with a detectable gap between each type of test element in the container. Preferably the container is conveniently in the form of a sleeve of test elements and each test element is independently accessible. The test elements are located in slots in the sleeve and the detectable gap is one or more slots containing no test element. The gap is detected by proximity sensing of the reflective difference between the presence and absence of a test element in a given slot. The container may also take the form of a rack or a support with positioning guides for holding test elements and the optical sensing would operate in like manner in that case detecting the reflective difference between the presence or absence of the foil wrapped consumable.

The herein described container and method provide considerable time savings and improvements in throughput when used in conjunction with an automated apparatus, as the inventory function makes possible random access to a greater number of types of test elements loaded within a single sleeve.

These and other features and advantages will become readily apparent from the following Detailed Description, which should be read in conjunction with the accompanying drawings.

DETAILED DESCRIPTION

The following discussion relates to certain exemplary embodiments of a method for holding multiple types of clinical immunodiagnostic, for instance, immunohematologic test elements such as cards or cassettes within single containers such as boxes or sleeves, and allowing random access to any such card or cassette in any container while permitting fast determination of card/cassette type inventory in all sleeves. It will be readily apparent to those of skill in the field that the inventive concepts described herein also relate to literally any other form of clinical analyzer that supports the functionality of multiple containers such as sleeves, racks or supports with positioning guides, containing test elements. In addition, certain terms are used throughout this discussion in an effort to provide a frame of reference with regard to the accompanying drawings. These terms should not be regarded as limiting, except where so specifically indicated.

For purposes of background, FIGS. 1 and 2 illustrate a pair of prior art immunodiagnostic test elements. More specifically, FIG. 1 depicts a gel card 20 while FIG. 2 depicts a glass bead cassette 30. Each of the test elements 20, 30 include a number of common structural features. That is, each test element 20, 30 commonly includes a support member 26 in the form of a planar substrate having a top side 27 and a bottom side 28, wherein the substrate supports a plurality of microtubes or test columns 34. The microtubes 34 are made from a transparent material and are further defines by an upper portion 37 having an open top opening, an inwardly tapering transition portion 39 and a lower portion 41. A predetermined quantity of an inert material 38, 42, is contained within the lower portion 41 of each test column 34, as typically provided by the manufacturer. In the instance of the gel card 20, the inert material 38 is a gel material, such as Sephacryl or other suitable material, while in the instance of the bead cassette 30, the inert material 42 is defined by a matrix of glass or other bead material. Each of the inert material 38, 42 is typically defined by a plurality of particles having a diameter of between about 10 and 100 microns. Typically, the inert material 38, 42 contained in each microtube 34 is further coated with an antibody or provided with a carrier-bound antigen or antibody, such as anti-A, also typically provided by the manufacturer, thereby defining an aqueous medium. At least fifteen (15) types of test elements are available, each for different immunological tests. A pierceable wrap conveniently comprising a foil wrap 50 provided at the top side 27 of each test element 20, 30 covers and seals the microtubes 34 in order to protect the contents and also to prevent dehydration or degrading thereof. Further advantages of this wrap in the practice of the instant invention are discussed hereinbelow.

Figure 3:
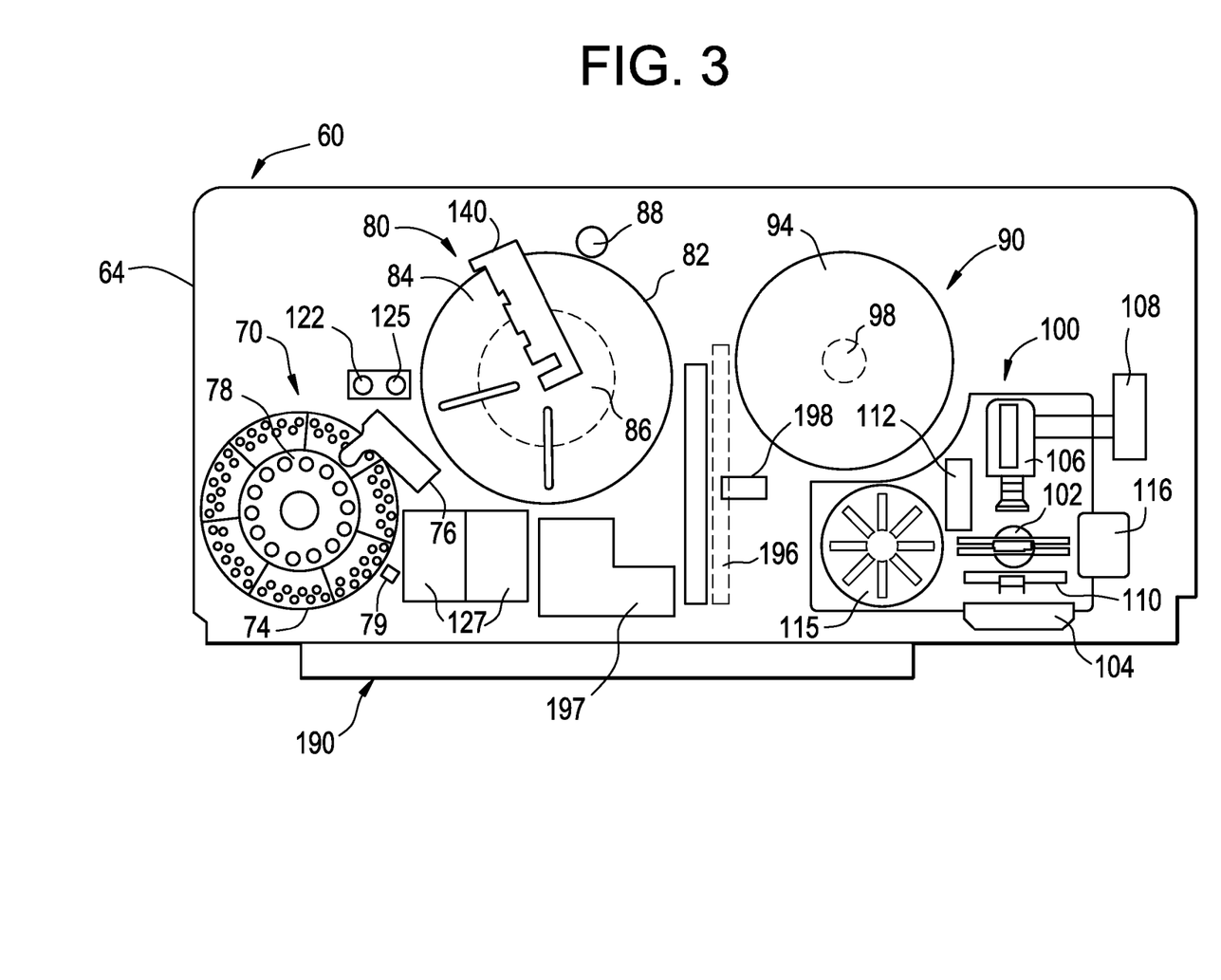
FIG. 3 is a partial top perspective view of a prior art immunodiagnostic testing apparatus.
Figure 4:
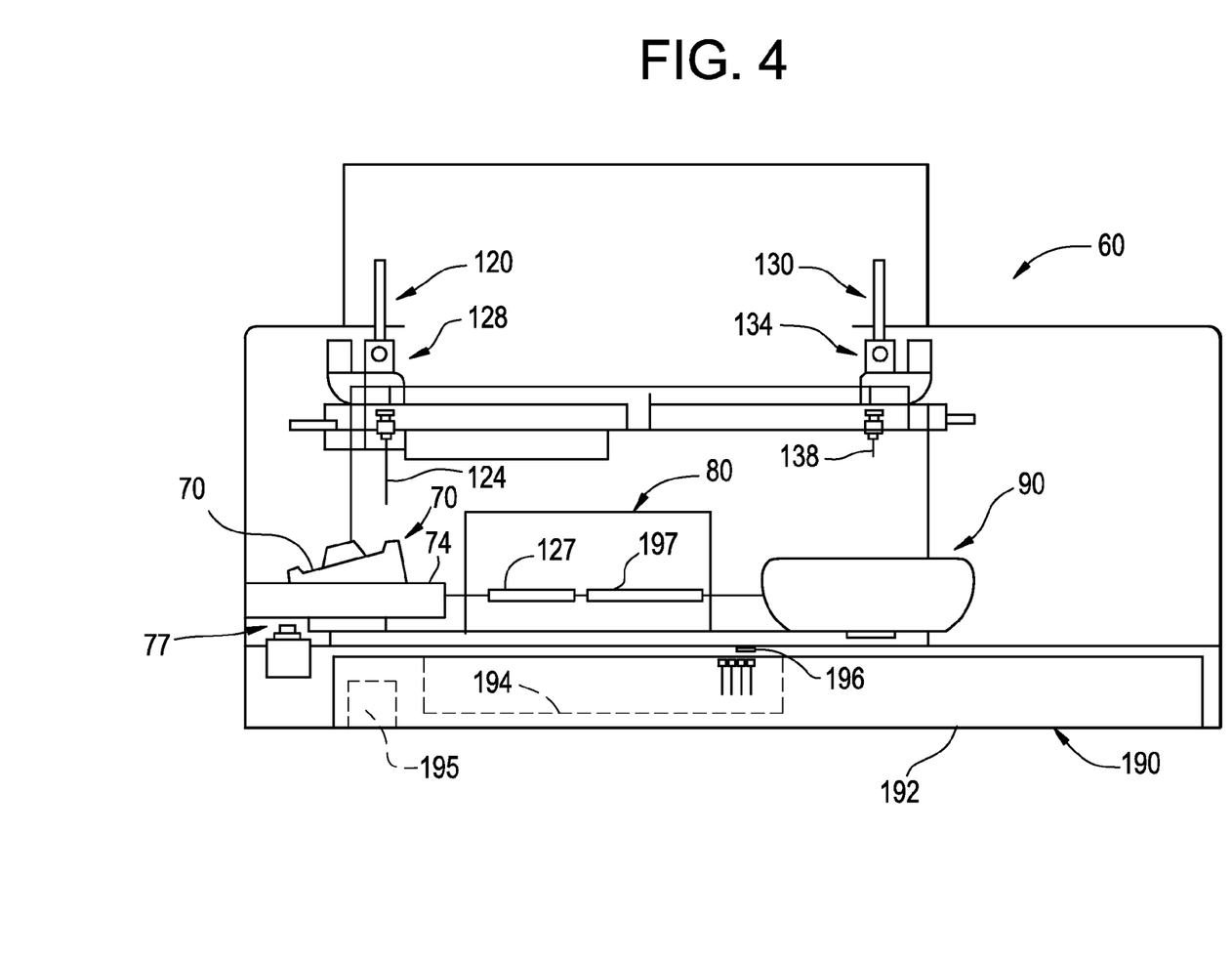
FIG. 4 is a simplified front view of the testing apparatus of FIG. 3.
Figure 5:
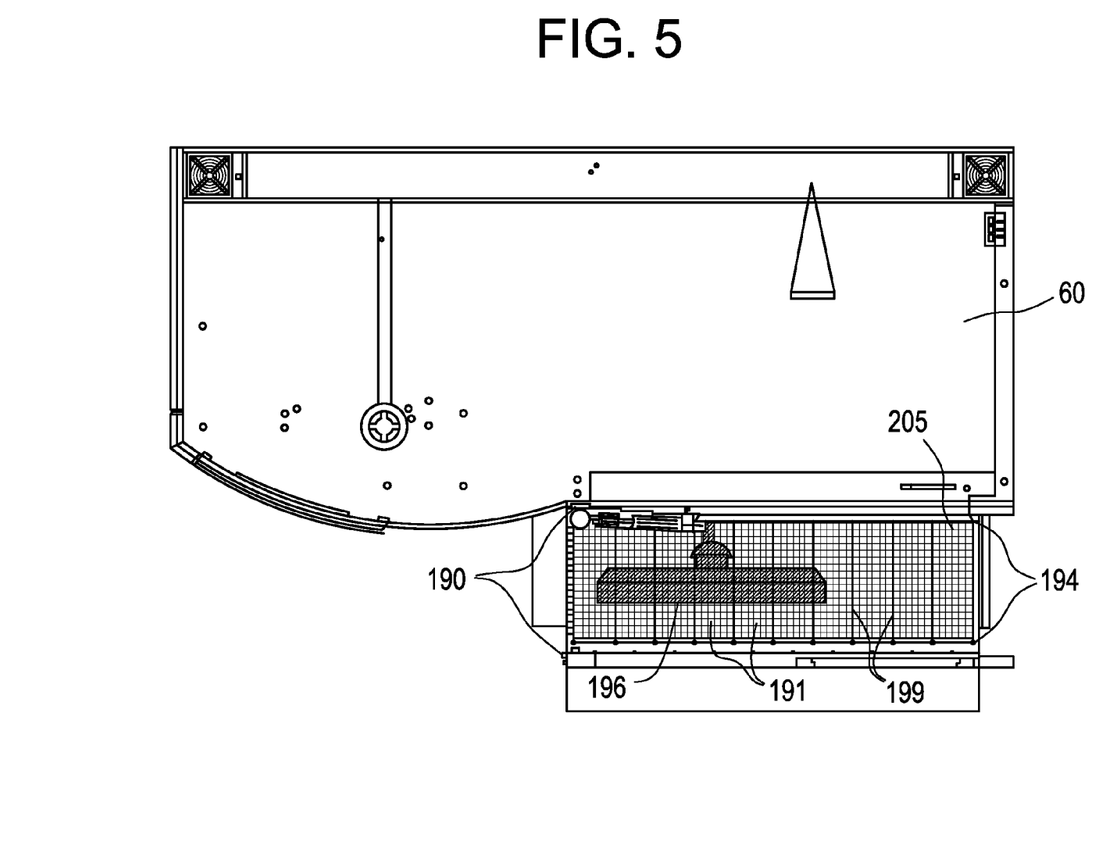
FIG. 5 is a simplified top perspective view of a prior art immunodiagnostic testing apparatus showing an open drawer.

Now with further reference to the accompanying Figures, it is described how the foregoing immunodiagnostic test elements 20, 30 can be used in an automated testing apparatus 60, such as that shown in FIGS. 3-5. Those skilled in the art of clinical laboratory blood analysis will understand the following description as exemplary of a clinical blood analysis apparatus. In brief, the testing apparatus 60 retains a number of components including a reagent and sample supply 70, an incubator station 80, a centrifuge 90, an analysis station 100, and a drawer assembly 190, each shown in FIG. 3. More particularly, the sample and reagent supply 70 of this apparatus 60 includes a sample rack 74 as well as a reagent rack 78, each of which contain bottles or vials of patient sample and reagent, respectively. The supply is constructed as a rotor that is rotatable about a center axis by means of a drive mechanism that includes a motor 77, FIG. 4, wherein a bar code reader 79, FIG. 3, is further provided in relation to the supply 70 as well as a tube hold-down assembly 76 disposed over a portion thereof. The incubator station 80 includes a cassette rack 82 that further includes respective first and second sections 84, 86, as well as a drive mechanism that includes a motor 88. The centrifuge 90 includes a rotor 94 and a motor 98. The analysis station 100 includes holding means 102, illumination means 104, an imaging subsystem 106, a processing subsystem 108, a transport subsystem 110, a storage rack 115, a bar code reader 112, and a waste receptacle 116. The drawer assembly 190, FIGS. 4 & 5, includes a drawer 192, a slide tray 194 which holds a number of sleeves 193, a motor 195, FIG. 4, a sensor bar 196, also shown in FIG. 5, a bar code reader 198, FIG. 4, and a holding area 197. A transport assembly 130, FIG. 4, of the testing apparatus 60 includes a robot arm 134, and a gripper 138. Finally, a pipette assembly 120, FIG. 4, includes a pipette 124 attached to a robot arm 128, this assembly further including shallow and deep wash areas 122, 125, as well as cell dilution packs 127.

Figure 6:
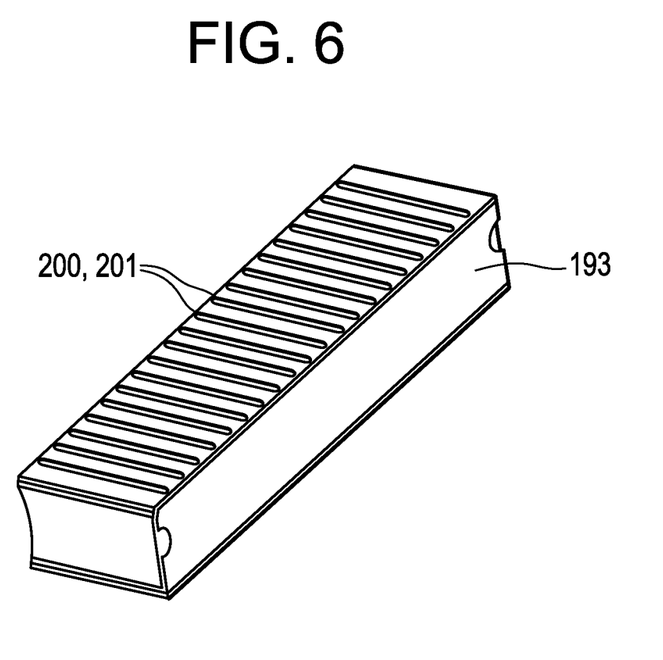
FIG. 6 is a schematic view of a sleeve.
Figure 7:
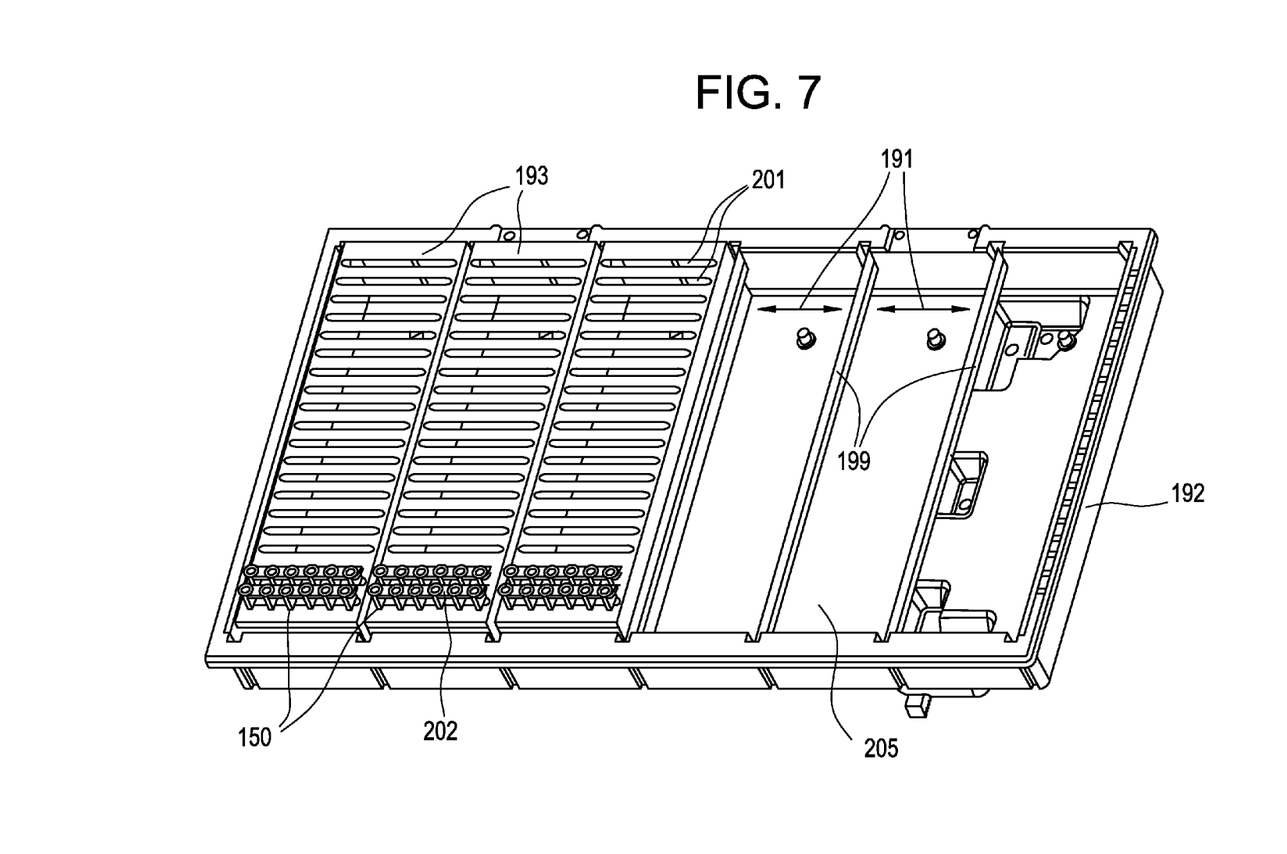
FIG. 7 is a schematic view of a slide tray showing sleeves with 20 compartments containing two test elements each placed in three lanes.

In one embodiment of the invention, a plurality of test elements 20, 30, such as those previously described according to either FIG. 1 or 2, are supplied by the manufacturer supported in sleeves 193, FIG. 6, containing compartments or slots 200 designed to accommodate the size and shape of individual test elements. Such sleeves are commonly made of paperboard or cardboard but can be made of any suitable material. The sleeves as commonly supplied contain twenty (20) immunohematologic test elements of a single type, such test elements positioned upright such that the foil wrap on the top of the test element is clearly visible at the top side. The sleeves 193 fit snugly in lanes 191, defined by the right and left sides of the drawer and by rails 199 positioned and affixed to the sides of the drawer (FIG. 7). Test elements 20, 30 are received from the manufacturer in such sleeves which are placed into the lanes 191 of the slide tray of an analyzer drawer in desired numbers up to the capacity of the drawer and ready for use in such immunohematologic tests as ordered by the physician. In the prior art, only one type of immunohematologic test element card/cassette could be loaded into a given sleeve as there was no functionality of inventorying and choosing a specific test element type from within a single sleeve. In the instant invention, more than one type of test element may conveniently be loaded into a single sleeve. To do so, the operator removes multiple test elements from a given sleeve as supplied by the manufacturer, and inserts test elements of a different type therefor, grouping all the test elements of a single immunohematologic test type into consecutive slots within the sleeve while leaving at least one slot empty between the two (or more) types of immunohematologic test elements. It is therefore to be understood that when the test element capacity of a sleeve is x, and when more than one type of test element is to be loaded into a sleeve, the number of test elements so loaded will be not greater than x−1, and test elements may be loaded starting at slot number 1 (placement as shown in FIG. 7). The operator will thus load test element(s) of another type of immunohematologic test into the same sleeve while leaving at least one slot empty between the two types of immunohematologic test elements. The empty slot(s) are location(s) where one or more test element(s) could otherwise be located, and functions as a detectable gap for the optical sensing bar 196, FIGS. 4 & 5, of the apparatus. The detectable gap is sensed by an optical proximity sensor through detection of the reflective difference of the presence or absence of a foil-wrapped consumable test element. Software in the sub-processor thus determines the inventory for the consumable test element of a given type. This aforementioned sleeve-loading continues for the multiple types of test elements as desired up to the capacity of the sleeve, and is repeated for all sleeves as desired, and up to the full capacity of the slide tray 194 within the drawer 192 at the CCLA of the apparatus 60, with at least one empty slot between each group of test elements of the same type.

In the embodiment wherein test elements are contained in sleeves, and once the operator has loaded the test elements 20, 30 of the various types as desired into the sleeves 193, FIGS. 5 & 6, and has left at least one empty slot 200 that serves as the detectable gap therebetween, the operator loads the sleeves into the lanes 191 of the slide tray 194 at the card/cassette loading area (CCLA), and closes the drawer 192. Upon any closure of drawer 192, whether due to loading of new sleeves or arranging or adding test elements within or to sleeves, for example each time the contents of the drawer are accessed and the drawer is thereafter closed, and also upon powering on of the apparatus 60, the sensor bar 196 scans all sleeves, detecting location of groups of test elements within a given sleeve and, where so loaded by the operator, separated from another group of test elements by at least one empty slot. It will be apparent that a "group" can consist of a minimum of a single test element of a given type and a maximum of x test elements wherein x is the test element capacity of the sleeve. As stated above, when more than one type of test element is loaded into a single sleeve, the groups of test elements will have at least one empty slot therebetween. Those having skill in the art will know of similar means to detect the test elements 20, 30 within the sleeves 193 resident in the slide tray 194, aside from that disclosed herein. The optical sensor bar 196 communicates with the processing subsystem 108 the difference between the reflectivity of the foil wrap and the reflective capacity of the bottom support member of the sleeve which contains no test element i.e., empty slots, or the lack of a test element in a slot, where any may exist, through proximity sensing. In the case where the operator has loaded a single sleeve with the same type of test element, the optical sensor 196 will so detect and using an appropriate algorithm the processing subsystem 108 thereby determines that one type of test element is so loaded. In the case where the optical sensor 196 through proximity sensing detects groups of test elements separated by at least one empty slot, using an appropriate algorithm the processing subsystem 108 determines that more than one different type of test element is present in a single sleeve 193. When the optical sensor bar 196 has detected the arrangement and presence or absence of test elements in the slots, and this has been done for all sleeves, the inventory function is complete and the arrangement of test elements is stored in the processing subsystem 108. As stated, this inventory function proceeds after each closure of the drawer 192 and after each power-on of the apparatus.

Figure 8:
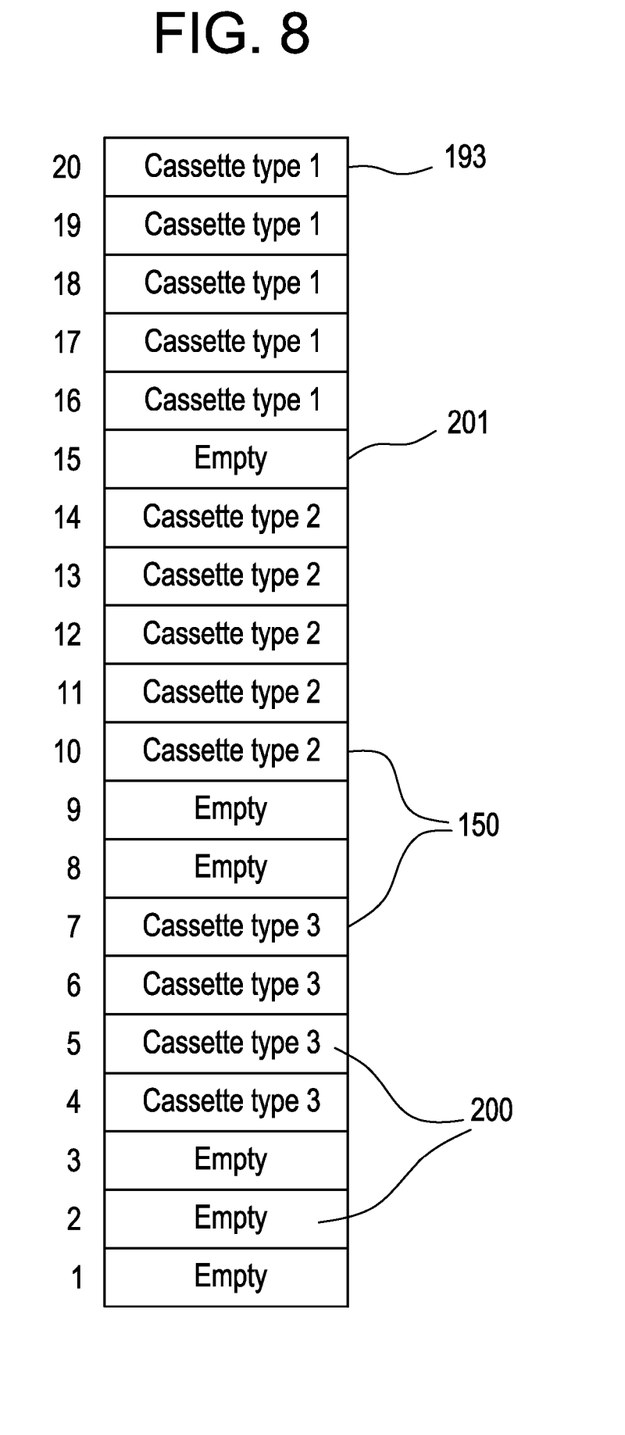
FIG. 8 is a plan view of immunodiagnostic test elements arranged in a sleeve with 20 compartments containing three types of test element, one for each of three types of clinical immunohematologic tests, with test elements of different types of clinical immunohematologic tests separated by a gap of at least one empty slot.

When the optical sensor bar has completed scanning and the results are stored in the processing subsystem, a software algorithm instructs the gripper arm 138, FIG. 4 of the holding means 102, FIG. 3, to grip the first test element of each group in a sleeve. The first test element of a group is the test element in any group closest to an operator standing at the front side of the apparatus 60, and are thus numbered 1-20 in FIG. 8. With reference to FIG. 8, test element position number ascends counting from front to back of the apparatus. With reference to FIG. 8, the first test element the gripper will pick is that test element in the number 4 position. The gripper arm 138 places that test element before illumination means 104 whereby the barcode on the single test element is read by the imaging subsystem 106. The type of test element 20, 30 in that entire group is thereby determined, along with other barcode information on the test element which, as stated above, can include the particular immunohematologic test type, shelf expiration, lot number, and the sequence of that test element within a given lot, among any other indicating information contained in the manufacturer's barcode. This information is then made visible to the operator on the Graphical User Interface or GUI. The information can include for example whether a particular scanned test element is expired or recalled, alerting the operator to deny usage of that card and automatically transport that card to the waste receptacle 116.

The gripper arm, having thus transported the first test element in a first group of test elements and returned that test element to its slot, proceeds to the next group of test elements in the sleeve that are separated by at least one empty slot, as previously detected by proximity sensing by the optical sensor 196 as a detectable gap and stored in the processing subsystem. This information is employed by the processing subsystem to advance the gripper arm to the next group of test elements separated from another group of test elements separated by at least one empty slot, where this configuration may exist in any sleeve. With reference again to FIG. 8, the gripper will then pick the test element is slot numbered 10, and place it before the barcode reader, which reads the barcode information prior to the gripper arm returning the test element to position 10. This activity continues routinely for all groups of test elements within each sleeve, allowing for complete inventorying of the test element contents of each sleeve resident in the drawer assembly 190 of the apparatus 60. The inventory function for the various types of test elements within the sleeve is thus achieved and the result of the inventorying function is displayed on the GUI for the operator. Depending on the contents of the sleeve and the test element required for a given test ordered by the physician, the operator may open the drawer and load appropriate types of test elements into the sleeves. Where the processing subsystem 108 includes a database or is connected remotely to a Laboratory Information System (LIS) replacement test elements are automatically ordered from a manufacturer or requisitioned for example from another location within a hospital or laboratory as they are used by the apparatus and/or ordered via automated functionality by physicians.

Figure 9:
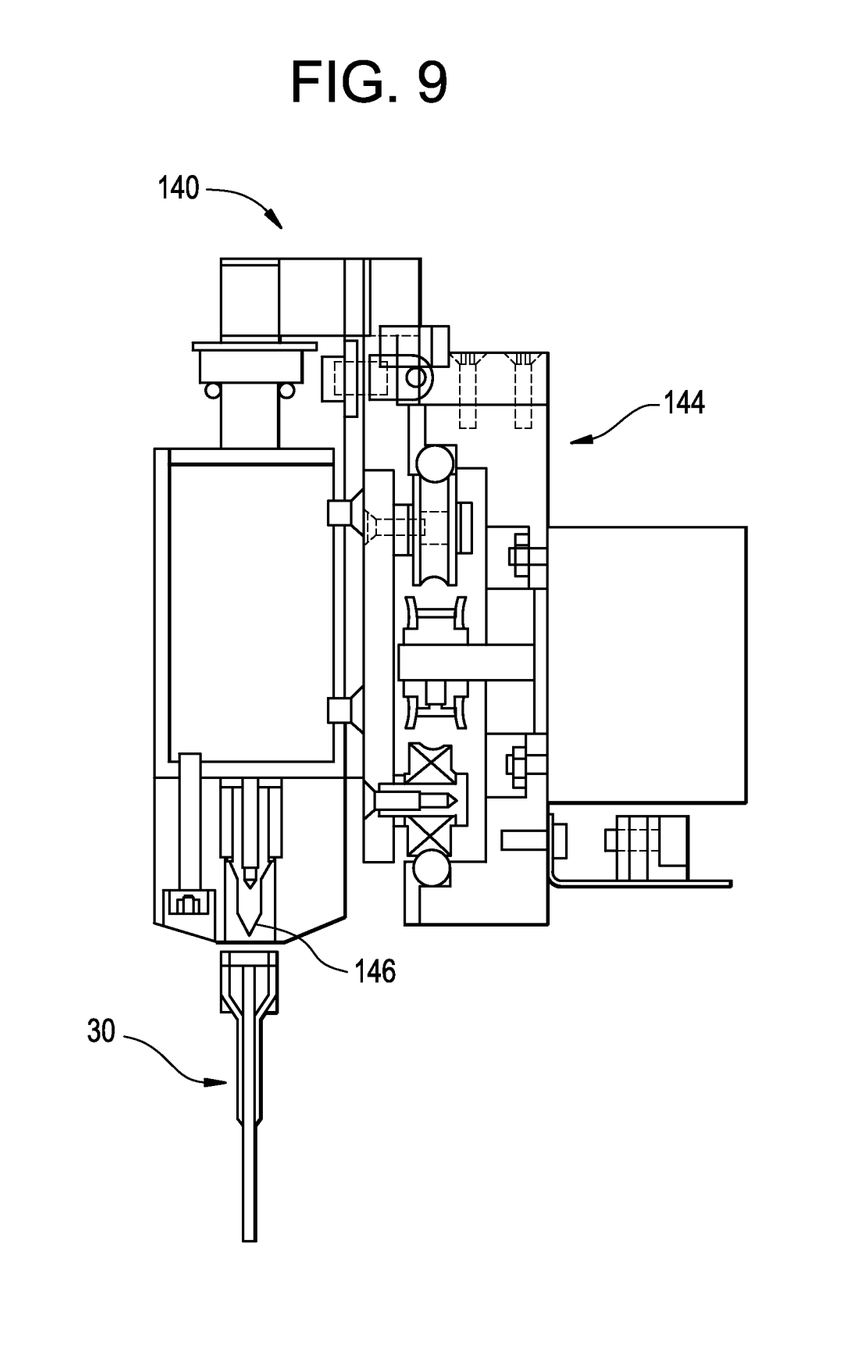
FIG. 9 is a partial side elevational view of the piercing assembly of the prior art immunodiagnostic testing apparatus of FIG. 3
Figure 10:
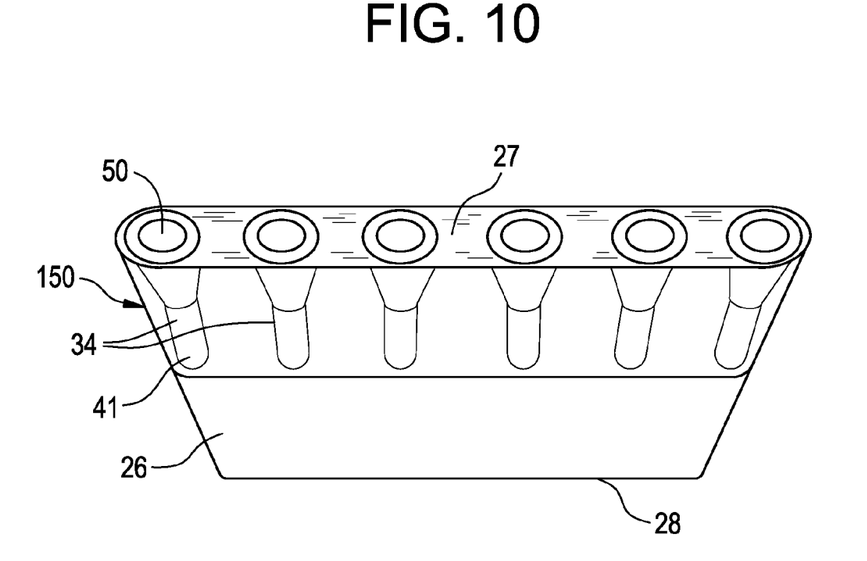
FIG. 10 depicts a top perspective view of a test element bearing a foil wrap closing the top side of the test element.

Once the inventorying function including the test element(s)' identification by barcode reader is complete, and the operator calls for an immunohematologic test, the gripper loads an appropriate test element depending on the test to be conducted into the cassette rack 82 of the incubator 80. A piercing assembly 140, FIG. 9, is disposed above the first and second sections 84, 86 of the cassette rack 82 of the incubator 80 and includes a support subassembly 144 that includes a slide support 145, FIG. 9 (not labeled), having a plurality of puncture needles (not shown) that are reciprocably movable, such as by means of solenoids (not shown). The pipette 124 of the pipette assembly 120 is used to aspirate sample from the sample rack 65, while the piercing assembly 140, FIG. 9, is used to puncture the foil wrap above each of the microtubes of the then-incubated test elements 20, 30, FIG. 10. Once the puncturing step has been completed as shown by the test elements, the pipette 124 can then be used to dispense a predetermined quantity of patient sample (and possibly additional reagents) from the sample and reagent supply 70 into each of the test columns 34, FIGS. 1 & 2, wherein the mixture can be suitably incubated. The incubator 80, as driven by the motor 88, is used to incubate patient sample added to each of the test columns from one of the vials of the sample rack 65, the incubator further including an assembly 76 that holds down the sample and reagent vials.

One having skill in the art will understand that alternative embodiments to the sleeve may include use of a container such as a rack, said rack designed to hold multiple test elements in the appropriate orientation wherein there is left at least one open space between the test elements. In a further embodiment, the floor 205 of the slide tray 194 may have guides or dividers to support the individual test elements themselves in the appropriate orientation, and wherein the operator would in like fashion leave at least one open space or slot between the types of test elements.

Following incubation and in the described testing apparatus 60, the test elements 20, 30 are removed from the incubator 80 by means of the transport assembly 130 to the centrifuge 90 wherein the test elements 30 are then spun down, thereby accelerating an agglutination reaction as red blood cells are clumped together in the presence of coated reagents. The plurality of beads disposed in each column of the test element 30 includes particles having diameters ranging between about 10 and 100 microns, providing a matrix for the red blood cells, but not the heavier formed agglutinates to pass through by filtering. The resulting reaction can be imaged within the analysis station 100 of the apparatus 60 by means of the illumination assembly 104 and imaging subsystem 106, the latter being connected to the processing subsystem 108 having machine vision for grading of the reaction. Additional details concerning the foregoing testing apparatus 60 are provided in commonly-assigned U.S. Pat. No. 5,578,269, to Yaremko et al., the entire contents of which are herein incorporated by reference.

As has been discussed in detail hereinabove, the functionality disclosed permits the apparatus 60 to quickly scan inventory of various test element types by reading a single test element from a group rather than reading test elements individually, thus supporting multiple types of test elements within a single sleeve and random access to each and thereby providing an efficient inventory of test element in an apparatus.

PARTS LIST FOR FIGS. 1-13

20 gel card
26 support member (planar substrate)
27 top side
28 bottom side
30 bead cassette
34 microtubes (test column)
37 upper portion
38 gel material
39 inwardly tapering transitional portion
41 lower portion
42 bead matrix
50 foil wrap
54 label
55 bar code
58 panel
60 automated testing apparatus
64 frame
70 sample and reagent supply
74 sample rack
76 tube hold-down assembly
77 drive means
78 reagent rack
79 bar code reader
80 incubator station
82 cassette rack
84 first section
86 second section
88 motor
90 centrifuge
94 rotor
98 motor
100 analysis station 102 holding means
104 illumination means
106 imaging subsystem
108 processing subsystem
110 transport subsystem
112 bar code reader
115 storage rack
116 waste receptacle
120 pipette assembly
122 shallow wash area
124 pipette
125 deep wash area
127 cell dilution racks
128 robot arm
130 transport assembly
134 robot arm
138 gripper
140 piercing assembly
144 support subassembly
146 piercing needles
150 test element
154 weakened or pre-stressed portions
170 punch
176 punch head
180 metering tip member
181 direction
182 cylindrical body
183 sample
184 upper tip opening
186 lower tip opening
188 interior
189 metering mechanism
190 drawer assembly
191 lane
192 drawer
193 sleeve
194 slide tray
195 motor
196 sensor bar
197 holding area
198 bar code reader
199 rail
200 slots in a sleeve
201 empty slot
202 foil wrap at top side of test element
205 floor of slide tray It will be understood that numerous variations and modifications are possible within the ambits of the inventive concepts described herein, as provided in the following claims.

The invention claimed is:

1. A method of determining test elements of multiple types stored in a clinical analyzer, said method comprising:
    positioning groups of test elements in a container disposed in a drawer of the clinical analyzer, the container comprising at least one sleeve, rack or support with positioning guides;
    closing the drawer of the analyzer, wherein the closing of the drawer energizes an optical sensor bar disposed within the analyzer;
    using the optical sensor bar of the analyzer, sensing test elements within the container containing multiple groups of test elements, wherein a gap capable of being sensed and detected by the optical sensor bar of the clinical analyzer is provided between each group of test elements positioned in the container, each of said test elements comprising an immunohematologic test card or cassette having a top surface including a foil wrap and in which the gap is detected based upon lack of a reflectance signal as measured by the optical sensor and indicative of an empty slot in the container;
    determining the type of test element within each group of test elements by sensing at least one of the elements within each group of test elements, each of said test elements including machine-readable information indicative of the type of test element and in which the determining step comprises the step of reading the machine-readable information within the clinical analyzer;
    generating data indicative of the number of test elements in each group and number of groups of multiple types of test elements from said sensing based on the detection of at the least one said gap by the optical sensor relative to the container; and
    using said generated data to provide a quantity of the multiple test elements stored in the clinical analyzer for each group of test elements,
    wherein at least the sensing and generating steps are automatically performed each time the analyzer drawer is opened and closed.

2. The method of claim 1, wherein the detectable gap is indicative of a slot where a test element would normally be located in the container.

3. The method of claim 1, wherein the sensing is optical proximity sensing.

4. The method of claim 3, wherein the result of the optical proximity sensing is stored in a processing subsystem of the clinical analyzer.

5. The method of claim 3, wherein said generating data step includes performing an algorithm that determines a change in number of test elements in the group in the container from previously stored data in the number of test elements in the group in the container.

6. The method according to claim 1, further comprising:
    retrieving a previous indication of the number of test elements in the group in the container;
    determining a change in the number of test elements in the group in the container to a new number of test elements in the group in the container in the step of generating;
    associating the change in the number of test elements in the group in the container to a usage indication; and
    storing the association.

7. The method of claim 6, further comprising notifying a user with an indication of the change in the number of test elements in the group in the container.

8. The method of claim 7, wherein the indication is selected from the group comprising a visual indication or an audible indication.

9. A method for providing random access to multiple types of consumables in a container which is configured for use in a clinical analyzer, the consumables including a plurality of immunohematologic test elements comprising at least one of test cards or cassettes, each test element having a top surface that includes a reflective foil wrap:
    arranging each type of test element in a group within slots within the container,
    spacing each group of test elements of a first type from another group of test elements of a second type by a detectable gap, in which the detectable gap is representative of at least one empty slot detectable by an optical sensor in the clinical analyzer based on reflective differences between the foil wrap of a test element and the at least one empty slot, closing the drawer of the analyzer, which automatically energizes the optical sensor;

sensing the presence of all detectable gaps of the container and generating data representative of each group of test elements, wherein at least one test element of each group of test element is designated with a marking indicative of the test to be performed on the test element by the clinical analyzer; and randomly accessing at least one test element from a group of test elements in the container, as needed, for testing within the analyzer wherein a number of available test elements of each group of test elements is incremented and in which the opening and closing of the drawer causes the sensing and generating steps to be repeated.

10. The method of claim 9, wherein the container is a sleeve, a rack, or a support with positioning guides.

11. The method of claim 9, wherein each type of test element is configured for conducting an immunohematologic agglutination assay.

12. A container for storage and use in a clinical analyzer, the container comprising:

a sleeve, a rack, or positioning guides defining a plurality of slots configured for retaining multiple types of test elements each arranged together in the container according to its type within a drawer of the clinical analyzer, each test element being one of a test cassette and a test card, each test element having a reflective foil wrap on a top surface and a label comprising type of test element information; and a detectable gap between each type of test element provided by an empty slot of the container, the gap being detectable by an optical sensor in the clinical analyzer upon closure of the drawer of the analyzer based on reflective differences between the foil wrap of a test element and the gap and the type of test to be performed on the test element being detectable by an optical scanner based on imaging of the label, wherein a result of the optical sensor is stored in a processing subsystem of the clinical analyzer, and wherein the optical sensor is operable to detect the gap when the clinical analyzer drawer is closed.

13. The container of claim 12, wherein each test element is independently accessible.

* * * * *